(12) United States Patent
Wallach et al.

(10) Patent No.: US 12,220,591 B2
(45) Date of Patent: *Feb. 11, 2025

(54) AUTOMATED EXTERNAL DEFIBRILLATOR SYSTEMS WITH OPERATION ADJUSTMENT FEATURES ACCORDING TO TEMPERATURE AND METHODS OF USE

(71) Applicant: HeartHero, Inc., Denver, CO (US)

(72) Inventors: Clifford H. Wallach, Buffalo Grove, IL (US); Michael C. Garrett, Wilmette, IL (US)

(73) Assignee: HeartHero, Inc., Denver, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/416,482

(22) Filed: Jan. 18, 2024

(65) Prior Publication Data

US 2024/0181268 A1 Jun. 6, 2024

Related U.S. Application Data

(60) Division of application No. 17/819,796, filed on Aug. 15, 2022, now Pat. No. 11,883,676, which is a continuation of application No. 17/501,616, filed on Oct. 14, 2021, now Pat. No. 11,413,467.

(60) Provisional application No. 63/091,681, filed on Oct. 14, 2020.

(51) Int. Cl.
*A61N 1/39* (2006.01)
(52) U.S. Cl.
CPC ......... *A61N 1/3904* (2017.08); *A61N 1/3937* (2013.01); *A61N 1/3981* (2013.01); *A61N 1/3993* (2013.01)

(58) Field of Classification Search
CPC ... A61N 1/3904; A61N 1/3937; A61N 1/3981
See application file for complete search history.

(56) References Cited

U.S. PATENT DOCUMENTS

| | | | | |
|---|---|---|---|---|
| 5,454,710 A | * | 10/1995 | Landau | H01M 10/48 429/93 |
| 5,868,792 A | * | 2/1999 | Ochs | A61N 1/3904 607/27 |
| 5,869,970 A | * | 2/1999 | Palm | A61N 1/378 607/28 |

(Continued)

*Primary Examiner* — Eric D. Bertram
(74) *Attorney, Agent, or Firm* — Avek IP, LLC

(57) ABSTRACT

The disclosure describes various aspects of an automated external defibrillator (AED) system, including shock generating electronics, a battery configured for providing power to the shock generating electronics, power management circuitry configured for managing the shock generating electronics and the battery, at least one environmental sensor configured for monitoring environmental conditions in which the AED system is placed, and a controller configured for controlling the power management circuitry and the at least one environmental sensor. The at least one environmental sensor includes a temperature sensor configured for providing a temperature measurement, and the controller is further configured for adjusting operations of the power management circuitry in accordance with the temperature measurement provided by the temperature sensor. The disclosure further describes associated methods of using the AED system.

8 Claims, 3 Drawing Sheets

(56) References Cited

U.S. PATENT DOCUMENTS

| | | | | |
|---|---|---|---|---|
| 5,897,576 | A * | 4/1999 | Olson | A61N 1/3904 607/7 |
| 5,904,707 | A * | 5/1999 | Ochs | A61N 1/3925 607/6 |
| 5,944,741 | A * | 8/1999 | Ochs | A61N 1/3925 607/5 |
| 5,964,786 | A * | 10/1999 | Ochs | A61N 1/3925 607/29 |
| 6,005,370 | A * | 12/1999 | Gustavson | H02J 7/345 320/137 |
| 6,185,456 | B1 * | 2/2001 | Garrett | A61N 1/3931 607/6 |
| 6,191,560 | B1 * | 2/2001 | Sakakibara | H02J 7/007184 320/137 |
| 6,211,655 | B1 * | 4/2001 | Hardie | H02J 7/007194 320/150 |
| 11,413,467 | B2 * | 8/2022 | Wallach | A61N 1/3975 |
| 11,883,676 | B2 * | 1/2024 | Wallach | A61N 1/3981 |
| 2004/0186519 | A1 * | 9/2004 | Norton | A61N 1/3975 607/5 |
| 2007/0024246 | A1 * | 2/2007 | Flaugher | H02J 7/007192 320/150 |
| 2009/0008374 | A1 * | 1/2009 | Fosbinder | B23K 9/10 219/133 |
| 2009/0248128 | A1 * | 10/2009 | Nassif | A61N 1/046 607/142 |
| 2012/0190969 | A1 * | 7/2012 | Kameli | A61N 1/39624 607/29 |
| 2012/0256752 | A1 * | 10/2012 | Musser | H02J 7/04 340/636.2 |
| 2013/0304147 | A1 * | 11/2013 | Aoyama | A61N 1/3937 455/66.1 |
| 2015/0265844 | A1 * | 9/2015 | Powers | A61N 1/3943 607/6 |
| 2015/0321020 | A1 * | 11/2015 | Gumbrell | A61N 1/3925 607/5 |
| 2016/0214490 | A1 * | 7/2016 | Soo | B60L 58/12 |
| 2017/0003356 | A1 | 1/2017 | Kaib et al. | |
| 2018/0140859 | A1 * | 5/2018 | Meir | A61N 1/3993 |
| 2018/0169426 | A1 | 6/2018 | Montague et al. | |
| 2019/0308011 | A1 * | 10/2019 | Secilmis | A61N 1/3925 |
| 2019/0379212 | A1 * | 12/2019 | Cho | G06N 3/088 |
| 2019/0386351 | A1 * | 12/2019 | Kim | H02J 7/007192 |
| 2020/0069953 | A1 | 3/2020 | Finch et al. | |
| 2020/0373779 | A1 * | 11/2020 | Arizono | H01M 10/486 |

\* cited by examiner

AUTOMATED EXTERNAL DEFIBRILLATOR SYSTEMS WITH OPERATION ADJUSTMENT FEATURES ACCORDING TO TEMPERATURE AND METHODS OF USE

CROSS REFERENCE TO RELATED APPLICATIONS

This application is a division of U.S. patent application Ser. No. 17/819,796 filed Aug. 15, 2022, now U.S. Pat. No. 11,883,676, which is a continuation of U.S. patent application Ser. No. 17/501,616 filed Oct. 14, 2021, now U.S. Pat. No. 11,413,467, which claims the benefit of U.S. Provisional Patent Application Ser. No. 63/091,681 filed Oct. 14, 2020, all entitled "Automated External Defibrillator Systems With Operation Adjustment Features According To Temperature And Methods Of Use", the disclosures of which are herein incorporated by reference in their entirety.

FIELD OF THE DISCLOSURE

Aspects of the present disclosure generally relate to automated external defibrillators (AEDs) and, more particularly, to compact AED systems.

BACKGROUND OF THE DISCLOSURE 86 million Americans have risk factors for sudden cardiac arrest (SCA), while 12 million are at high risk. Cardiac events represent more deaths in America than breast, lung, colon and prostate cancer combined. More than 360,000 sudden cardiac arrest (SCA) occur outside of the hospital each year. According to the American Heart Association, nearly 70 percent of these SCAs occur at home, out of reach of the lifesaving shock of an AED.

As each minute passes following a sudden cardiac arrest, the chances of survival decrease significantly. If an AED is not applied within 10 minutes of a SCA event, chances of survival decrease to less than 1%.

One approach to increasing the chance of survival for SCA sufferers is to make AEDs more readily available and accessible for more people. However, the AEDs currently available on the market tend to be heavy, not portable, expensive, and intimidating to use for people without medical training. For example, US Pat. Pub. No. US 2018/0169426, entitled "Automatic External Defibrillator Device and Methods of Use," which disclosure is incorporated herein in its entirety by reference, provides a possible solution to overcome the availability and accessibility problem by providing a compact AED device suitable for portability.

Aspects of the present disclosure provide techniques and structures that improve the performance of AEDs suitable for high portability applications.

SUMMARY OF THE DISCLOSURE

The following presents a simplified summary of one or more aspects in order to provide a basic understanding of such aspects. This summary is not an extensive overview of all contemplated aspects, and is intended to neither identify key or critical elements of all aspects nor delineate the scope of any or all aspects. Its purpose is to present some concepts of one or more aspects in a simplified form as a prelude to the more detailed description that is presented later.

In an aspect, an automated external defibrillator (AED) system is described, in accordance with an embodiment. The AED system includes shock generating electronics, a battery configured for providing power to the shock generating electronics, power management circuitry configured for managing the shock generating electronics and the battery, at least one environmental sensor configured for monitoring environmental conditions in which the AED system is placed, and a controller configured for controlling the power management circuitry and the at least one environmental sensor. The at least one environmental sensor includes a temperature sensor configured for providing a temperature measurement, and the controller is further configured for adjusting operations of the power management circuitry in accordance with the temperature measurement provided by the temperature sensor.

In another aspect, a method for using an external defibrillator (AED) system is described, in accordance with an embodiment. The AED system includes shock generating electronics, a battery configured for providing power to the shock generating electronics, power management circuitry configured for managing the shock generating electronics and the battery, at least one environmental sensor for monitoring environmental conditions in which the AED system is placed, and a controller configured for controlling the power management circuitry and the at least one environmental sensor. The method includes measuring a temperature of the AED system, and adjusting operations of the power management circuitry in accordance with the temperature so measured.

BRIEF DESCRIPTION OF THE DRAWINGS

The appended drawings illustrate only some implementations and are therefore not to be considered limiting of scope.

DETAILED DESCRIPTION

Figure 1:
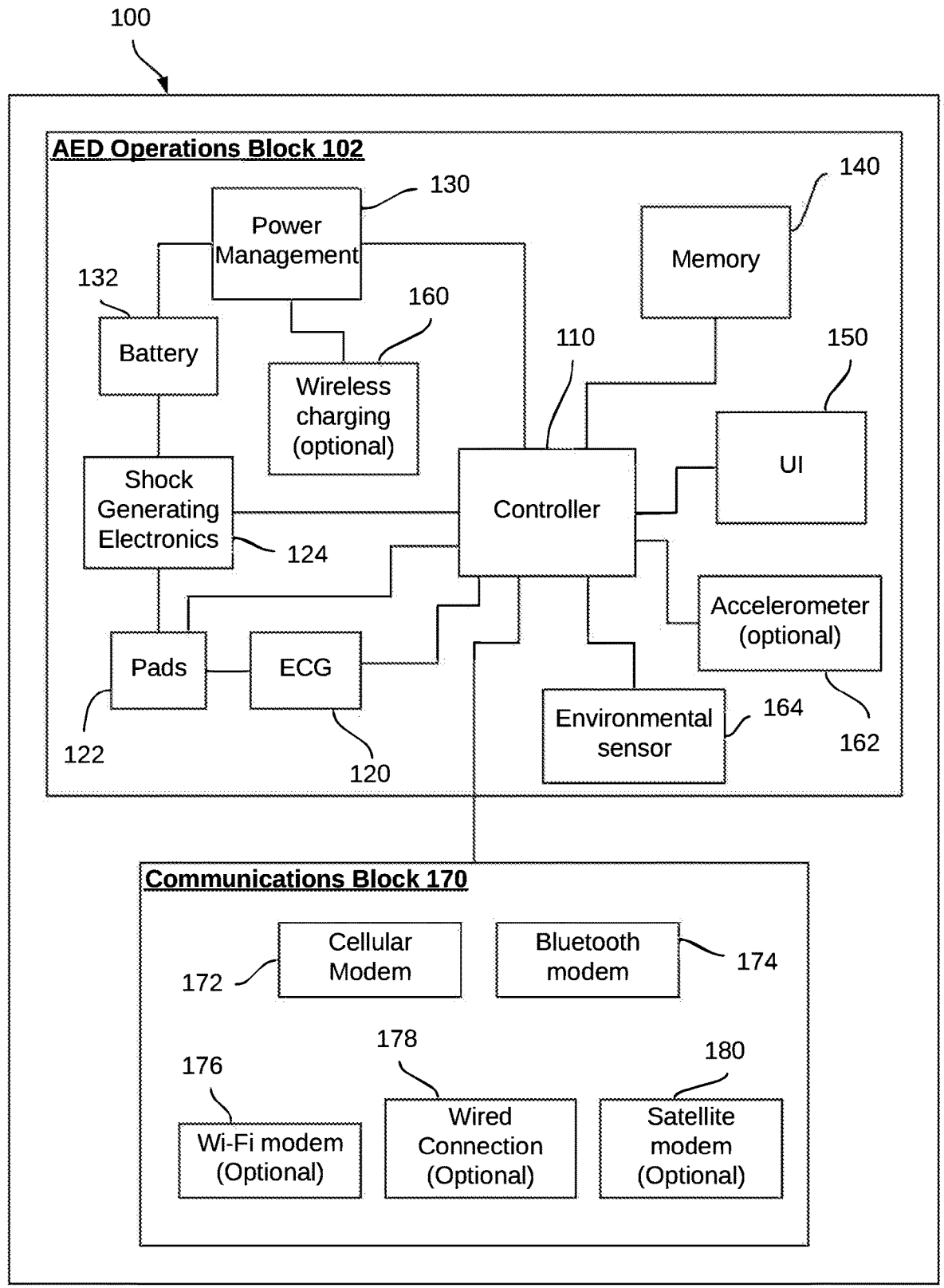
FIG. 1 illustrates a block diagram of an exemplary AED, including an AED operations block and a communications block, in accordance with an embodiment.

The present invention is described more fully hereinafter with reference to the accompanying drawings, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. In the drawings, the size and relative sizes of layers and regions may be exaggerated for clarity. Like numbers refer to like elements throughout.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" or "under" other elements or features would then be oriented "above" the other elements or features. Thus, the exemplary terms "below" and "under" can encompass both an orientation of above and below. The device may be otherwise oriented (rotated 90 degrees or at other orientations) and the spatially relative descriptors used herein interpreted accordingly. In addition, it will also be understood that when a layer is referred to as being "between" two layers, it can be the only layer between the two layers, or one or more intervening layers may also be present.

The terminology used herein is for the purpose of describing particular embodiments only and is not intended to be limiting of the invention. As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items, and may be abbreviated as "/"

It will be understood that when an element or layer is referred to as being "on," "connected to," "coupled to," or "adjacent to" another element or layer, it can be directly on, connected, coupled, or adjacent to the other element or layer, or intervening elements or layers may be present. In contrast, when an element is referred to as being "directly on," "directly connected to," "directly coupled to," or "immediately adjacent to" another element or layer, there are no intervening elements or layers present. Likewise, when light is received or provided "from" one element, it can be received or provided directly from that element or from an intervening element. On the other hand, when light is received or provided "directly from" one element, there are no intervening elements present.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and/or the present specification and will not be interpreted in an idealized or overly formal sense unless expressly so defined herein.

If more AEDs can be made available to more people, with improved portability, lower cost, and enhanced ease of use, then more lives can be saved in the event of an SCA occurring outside of a hospital setting. That is, like an EpiPen® injector is prescribed for and carried by those diagnosed with potentially life-threatening allergies, a portable AED can be a necessary and routine item prescribed to those diagnosed as being at risk for SCA. A portable, affordable, and user-friendly AED with safe and simple application protocol is desired for such wide-spread proliferation of AEDs in the consumer market. Additionally, secure and streamlined connections to emergency personnel, external data sources, and peripheral devices would also be desirable.

One challenge to having a portable AED is the necessity to ruggedize the AED such that the system can be stored and is operable in a variety of environmental conditions, such as at low and high altitudes, low and high humidity, and low and high temperatures (e.g., minus 20° C. to +50° C.). As the various components within the AED can function differently in different environmental conditions, and even the physical conditions of the patient (e.g., skin temperature) can impact the operation of the AED, it would be desirable for the portable AED to be able to adjust to varying environmental conditions during storage and in operation, preferably in real time.

Referring now to FIG. 1, an exemplary AED including an AED operations block and a communication block, in accordance with an embodiment, is illustrated. AED 100 includes features that allow AED 100 to be connected with the outside world so as to provide additional functionality and allow use scenarios that have been heretofore impossible. An AED 100 includes an AED operations block 102, which includes various components that enable AED 100 to generate and deliver, within regulatory guidelines, an electric shock to a person in Sudden Cardiac Arrest. As shown in the embodiment illustrated in FIG. 1, AED operations block 102 includes a controller 110, which regulates a variety of components including an electrocardiogram (ECG) monitoring circuitry 120, which is in turn connected with pads 122. Pads 122 are configured for attachment to specific locations on the SCA patient for both obtaining ECG signals and administering the electric shock generated by shock generating electronics 124, which is also controlled by controller 110. Controller 110 also monitors the condition of the pads, for example by measuring a face-to-face pads impedance. Increased pads impedance may indicate that the adhesives for attaching the pads to the SCA patient may be overly dry, thus requiring replacement to maintain effective operation of the AED system.

Additionally, AED operations block 102 includes a power management block 130, which is also controlled by controller 110 in an embodiment. Power management block 130 is configured for managing the power consumption by various components within AED operations block 102. For instance, power management block 130 monitors a charge status of a battery 132, which provides power to shock generating electronics 124. As such, controller 110 can alert the AED user if a low battery level is detected by power management block 130. Similarly, controller 110 can also regulate power management block 130 to control the on/off status of other components within AED 100 so as to minimize the power consumption by these other components while the AED is not being used. In an embodiment, for example, power management block 130 is configured to completely power down ECG monitoring circuitry 120 and shock generating electronics 124 when the AED is not being used. Controller 110 may include, for example, non-transitory memory for storing software instructions. The non-transitory memory may be communicatively coupled with a processor (e.g., microprocessor) for executing software instructions stored on the non-transitory memory. Software instructions may include, for instance, workflow information for operating the AED, as described herein.

Continuing to refer to FIG. 1, controller 110 is also connected with a memory 140, which stores information regarding AED 100, such as use history, battery status, shock administration and cardiopulmonary resuscitation (CPR) protocols, and other information (e.g., stored in look-up tables) used in the operation of AED 100.

Controller 110 further controls a user-interface (UI) block 150. UI block 150 includes, for example, voice and/or visual prompts for instructing the AED user on the use of AED 100 as delivered by a user interface, such as a haptic display such as a touch screen, light emitting diode (LED) indicators, liquid crystal display, speakers, switches, buttons, and other ways to display information to the user and/or for a user to control the AED. In an embodiment, UI block 150 can optionally include a microphone to receive voice inputs from the AED user. In an alternative embodiment, UI block 150 can optionally include an interface with an external application, such as a native or web app on a mobile device configured for communicating with AED 100.

AED Operations Block 102 as shown in FIG. 1 further includes optional features such as wireless charging circuitry 160 and accelerometer 162. For example, if a portion of battery 132 includes a rechargeable battery configured for wireless charging, then wireless charging circuitry 160 is used to charge the rechargeable battery. Optionally, power management block 130 can be used to control wireless charging circuitry 160 to trigger the battery charging process when the charge level of the rechargeable battery within battery 132 is detected to have fallen below a preset threshold. Alternatively, power management block 130 may trigger the battery charging process using a wired connection with an external power source (e.g., an electrical wall socket, car charger, or a power generator—not shown), when the charge level has fallen below a preset threshold. The optional accelerometer 162 may be used to determine whether the AED has been moved. If readings from the accelerometer indicate that the AED has been moved, an AED location check may be performed to determine new GPS coordinates and/or a temperature check may be performed using AED temperature sensors to determine environmental conditions at the new AED location.

Additionally, an environmental sensor block 164 can be used to monitor the environmental conditions in which AED 100 is placed. For instance, environmental sensor block 164 can include one or more of a temperature sensor, a hygrometer, an altimeter, and other sensors for monitoring the environments around AED 100 and/or one or more components within or coupled to the AED 100. As an example, environmental sensor block 164 monitors the temperature of battery 132 and/or pads 122, and/or the relative humidity of the environment in which the AED is placed.

Still referring to FIG. 1, AED 100 includes a communications block 170, also controlled by controller 110. Communications block 170 provides connections to external systems and entities outside of the AED, such as emergency medical services, hospital emergency rooms, physicians, electronic health record systems, as well as other medical equipment, such as ventilators and an external ECG. In an embodiment, communications block 170 optionally includes a cellular modem 172 and a Bluetooth® modem 174. Optionally, communications block 170 also includes, for example, a Wi-Fi modem 176 for providing wireless connection to and from an external device, one or more wired connections 178 for providing direct wired connection to AED 100 such as via a local area network (LAN), cable, phone line, or optical fiber. Communications block 170 can also optionally include a satellite modem 180 for providing remote communications via satellite. The various communication modes within communications block 170 are configured to comply with regulatory guidance related to wireless technology, such as coexistence, security, and electromagnetic compatibility. By having a single controller (e.g., a microprocessor) control the various blocks within AED 100, the circuit design and firmware configuration of AED 100 is greatly consolidated over other AEDs with multiple processors, while enabling a reduction in power consumption of the device.

Environmental conditions, such as temperature and humidity, affect both the performance of the AED in use and degradation rate of AED components during storage and transport. For example, it has been long recognized that the adhesives on the pads degrade more quickly at higher temperature such that others have suggested adjusting the regular replacement schedule of the pads according to the temperature conditions of the location at which the AED is stored and used, even without the AED and the pads having been deployed prior to replacement. Also, the batteries that power the AED operation have degradation rates that vary with temperature. For example, U.S. Pat. No. 6,980,859 to Powers, et al., mentions that the degradation rate of disposable batteries is similar to the degradation rate of the pads with respect to temperature.

Further, it is recognized herein that the particular temperature of the battery and pads can have implications on the safe operation of the AED, both during transport/storage and during shock delivery. By taking into account the ambient temperature and/or temperature at specific components within the AED, adjustments can be made by the power management module and/or by the controller within the AED operations block to enable safer and more reliable operation of the AED.

I. Accounting for Temperature in Battery Charge Level Assessment

The ambient or battery temperature can be taken into account in understanding the charge status of the battery. This temperature information can then be used to adjust the rate at which the shock generating electronics in the AED are charged. For example, the charge rate of the shock generating electronics may be reduced when the battery is at a cold temperature or at a low battery level in order to avoid a brownout situation where the controller and other circuits are not be able to function due to low power supply voltage from the battery.

Figure 2:
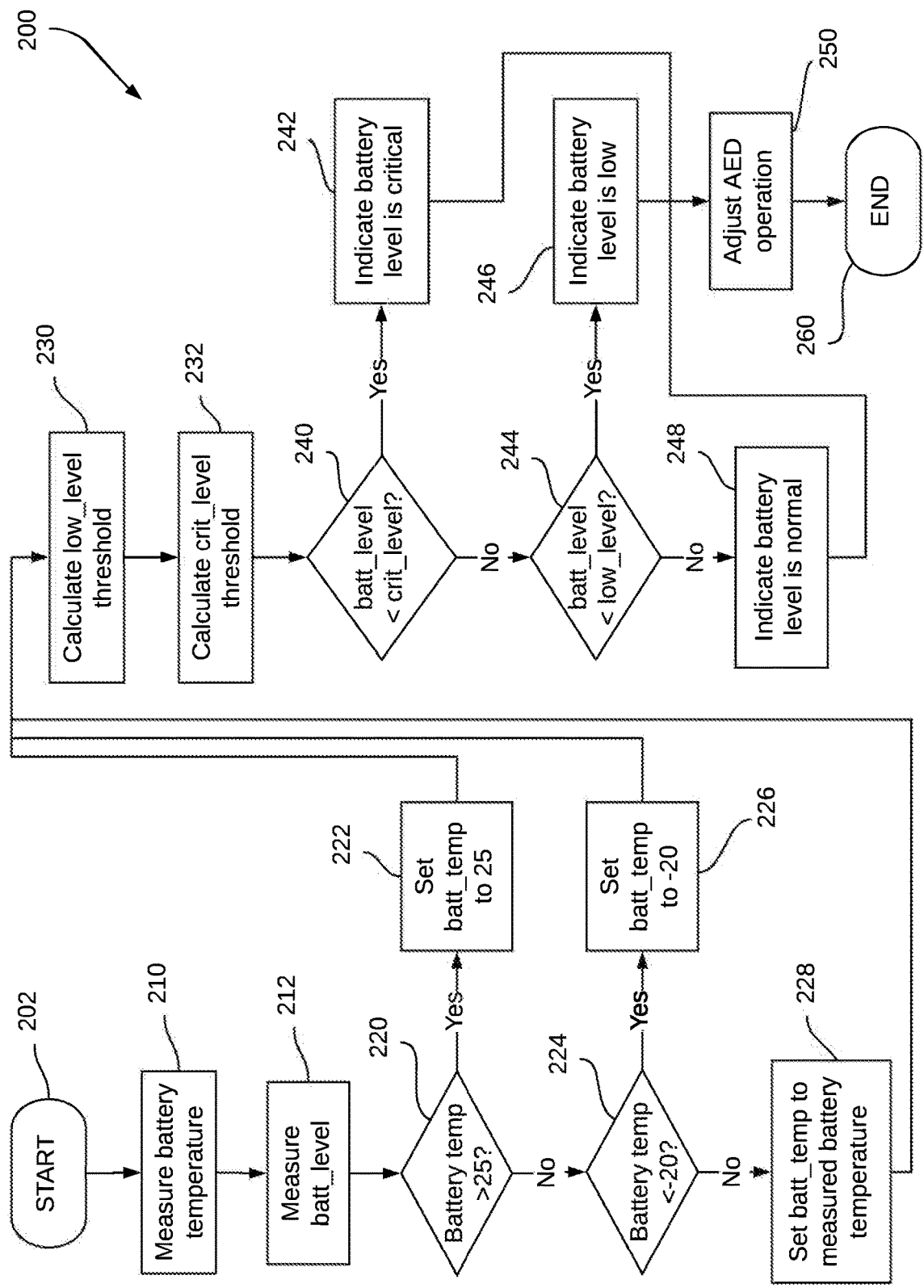
FIG. 2 illustrates a flow diagram of a process for adjusting the operation of an AED taking into consideration a measured battery temperature, in accordance with an embodiment.

An example of a process for using temperature data to adjust operations of the AED is shown in FIG. 2. A process 200 of FIG. 2 begins with a start step 202, followed by a step 210 to measure the temperature of the battery within the AED, such as battery 132 of AED 100. For example, environmental sensor block 164 may include a thermometer, a thermocouple, or thermistor device (e.g., a resistance temperature detector) for measuring the temperature of battery 132 and/or the external environment in which AED 100 is used. Optionally, the ambient temperature of the AED or another component within the AED may be used as a proxy for the battery temperature.

Process 200 proceeds to a step 212 to measure the voltage level ("batt_level") of the battery, thus providing an indication of how much charge can be provided by the battery at the time of interest (e.g., at the time the measurement is taken). For example, measurement of the voltage level of battery 132 can be performed by power management block 130.

TABLE 1

| | | Battery Level Thresholds (V) | |
| --- | --- | --- | --- |
| | | Low | Critical |
| Battery | 25° C. | 10.5 | 9.2 |
| Temperature | 0° C. | 8.6 | 8.0 |
| (° C.) | −20° C. | 7.6 | 6.8 |

In an example, a look-up table (e.g., TABLE 1 shown herein) can be used to determine specific battery level thresholds below which the battery voltage would be considered low or critically low. For example, if the battery voltage is determined to be low, then the AED controller may send a notification to a user. Due to the dependence of the measured battery voltage on battery temperature, it is recognized herein that the low and critically low battery level thresholds should be adjusted according to the battery temperature. Table 1 reflects an example set of threshold values considered suitable for effective operation of an exemplary AED. It should be noted that, while TABLE 1 shows the temperature values as measured at the battery, another temperature reading at a different portion of the AED, such as ambient temperature or the internal temperature of the AED case, may be used as proxy to the battery temperature. Threshold temperature levels may be adjusted depending on the location at which the temperature measurement is taken.

While the threshold values shown in TABLE 1 are for specific battery temperatures, a linear or nonlinear interpolation approach may be used to extend the data in TABLE 1 to temperatures below, above, and between the listed values. For example, a nonlinear regression (e.g., nonlinear least squares fittings) can be used to find a suitable function that best fits a given set of data points. An example approach can be found at http://www.xuru.org/rt/NLR.asp.

Returning to FIG. 2, a decision 220 is made to determine whether the measured battery temperature is greater than a high temperature threshold (e.g., 25° C.). If the answer to decision 220 is YES, then the value of variable batt_temp to be used in the threshold interpolation is set to the high temperature threshold value (e.g., 25° C.) in a step 222. If the answer to decision 220 is NO, process 200 proceeds to a decision 224, in which a determination is made whether the measured battery temperature is less than the low temperature threshold (e.g., −20° C.). If the answer to decision 224 is YES, then batt_temp is set to the low temperature threshold value (e.g., −20° C.) in a step 226. If the answer to decision 224 is NO, then batt_temp is set to the measured battery temperature value in a step 228.

From steps 222, 226, and 228, process 200 proceeds to a step 230, in which the voltage threshold value low_level (i.e., the voltage value below which the battery charge level would be considered to be too low for safe operation of the AED) is calculated for the given value of variable batt_temp. The equation used to calculate low_level takes into account the variable batt_temp as set in step 222, 226, or 228. As described above, this equation can be obtained by calculating an equation that fits the data given in TABLE 1. Similarly, in a step 232, the voltage threshold value crit_level (i.e., the voltage value below which the battery charge level would be considered to be critically low for safe operation of the AED) is calculated for the value of given variable batt_temp. Then a determination is made in a decision 240 whether the value of batt_level measured in step 212 is below the calculated voltage threshold value crit_level from step 232. If the answer to decision 240 is YES, then an indication is noted at the AED controller that the battery charge level is critically low in a step 242. If the answer to decision 240 is NO, then a determination is made in a decision 244 whether the value of batt_level is below the calculated voltage threshold value low_level from step 230. If the answer to decision 244 is YES, then an indication is noted at the AED controller that the battery charge level, while not critically low, is still considered low in a step 246. If the answer to decision 244 is NO, then an indication is noted at the AED controller that the battery charge level is normal at step 248. Following step 242, 246, or 248, the operation of the AED is adjusted according to whether the battery level is critically low, low, or normal in a step 250.

For instance, if the AED is actively in use to prepare to shock a patient, and the battery voltage level is determined to be low or critically low using process 200, then the power management block may slow the charge rate of the shock generating electronics to avoid quickly draining the battery. In another example, process 200 may take place during a self-test routine of the AED. In such a case, if the battery voltage level is low or critically low, then an alert may be sent to a registered user of the AED to recommend charging the AED battery as soon as possible. Alternatively, the power management block may automatically enable wired or wireless charging of the battery. Finally, process 200 is terminated in an end step 260.

While process 200 is shown with separate determinations for low and critically low battery levels, either one of these determinations may be eliminated for simplicity of calculation while staying within the scope of the present disclosure. Also, the specific values shown in TABLE 1 and used in the calculations in process 200 are exemplary only, and are not intended to be limiting. Process 200 may take place, for example, at controller 110 or power management block 130 of AED 100 in FIG. 1.

II. Estimate Pads Impedance Based on Temperature

Another way to take temperature into account during AED operation is in determining the status of the pads. As discussed earlier, the pads used in transmitting electric shock to a SCA patient degrade over time, and the pad degradation accelerates when stored at higher temperatures. One way to quantify pads degradation is by taking a face-to-face impedance measurement between the pair of pads. The face-to-face measurement process may include allowing electrical communication between faces of the two pads (e.g., by direct contact between portions of each face of the pads or by electrical coupling of a conductive wire between the faces of the two pads) and sending an electrical signal through the pads to determine an impedance theereof. Whereas temperature dependence of the pads impedance can be taken into account during AED use (i.e., when the pads are applied to a SCA patient) without explicit measurement and adjustment specifically for temperature because the voltage/current detection during the first fraction of a second of the shock delivery protocol takes any pads impedance variations into account, alternative current (AC) face-to-face measurements of the pads impedance, adjusted for temperature, can be used to check for pads degradation.

TABLE 2

| | | Pads Impedance (ohms) | | | | |
| --- | --- | --- | --- | --- | --- | --- |
| | | Pad Set #1 | Pad Set #2 | Pad Set #3 | Pad Set #4 | Pad Set #5 |
| Pads | 50° C. | 1.1 Ω | 2.1 Ω | 1.9 Ω | 0.9 Ω | 1.9 Ω |
| Temperature | 20° C. | 8.8 Ω | 8.9 Ω | 10.8 Ω | 9.1 Ω | 9.0 Ω |
| (° C.) | −20° C. | 166.2 Ω | 152.0 Ω | 160.2 Ω | 162.4 Ω | 151.0 Ω |

TABLE 2 shows the experimentally measured face-to-face impedance between exemplary pairs of pads at different temperatures. The face-to-face impedance of pads stored at a given temperature over one year increased only slightly after three years of storage at the same temperature. While elevated impedance measurement is an indication that the pads may be degraded, it is also recognized from the values in TABLE 2 that pads impedance measurements also increase at lower temperatures.

TABLE 3

| | | Pads Impedance Threshold (ohms) |
| --- | --- | --- |
| Pads Temperature | 25° C. | 40 Ω |
| (° C.) | −20° C. | 240 Ω |

Similar to the battery voltage level threshold determination, the pads impedance threshold values may be experimentally derived for specific use temperatures, then extrapolated using linear interpolation. TABLE 3 shows example values of empirically determined pads impedance threshold values at different temperatures. Then a linear interpolation may be used to adjust the pads impedance threshold value at temperatures between a low temperature threshold and a high temperature threshold (e.g., −20° C. and 25° C., respectively).

Figure 3:
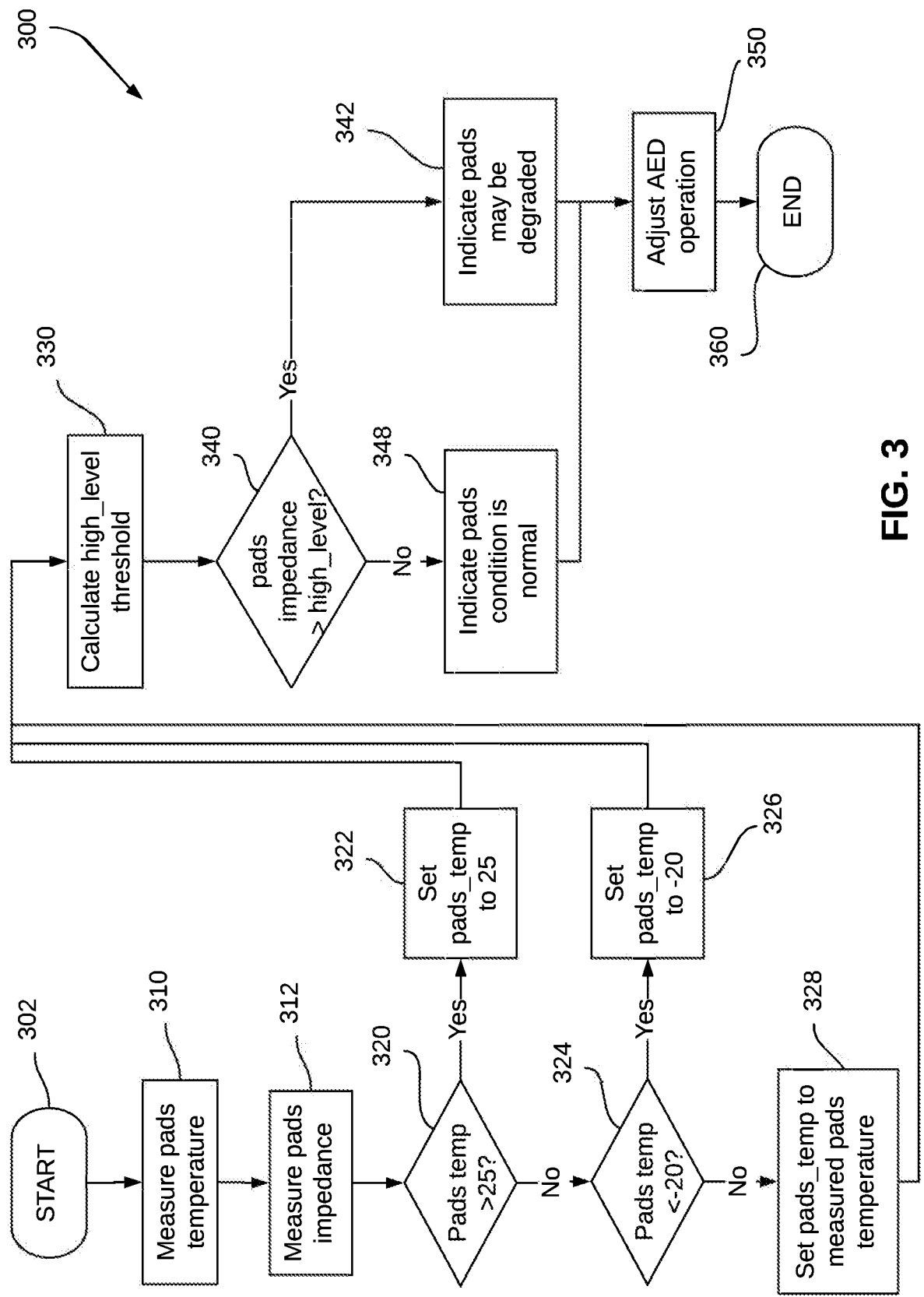
FIG. 3 illustrates a flow diagram of a process for adjusting the operation of an AED taking into consideration a measured pads temperature, in accordance with an embodiment.

An example of a process for adjusting the AED operation according to the determined condition of the pads is shown in FIG. 3. A process 300 of FIG. 3 begins with a start step 302, followed by a step 310 to measure the temperature of the pads stored with or within the AED. As described above with respect to the temperature measurement at the battery, the pads temperature measurement may be taken by environmental sensor block 164 of AED 100 shown in FIG. 1, and the ambient temperature or the temperature of another component within the AED may be used as a proxy for the pads temperature. Process 300 then proceeds to measure the pads impedance (i.e., face-to-face impedance measurement) of the pads in a step 312. The pads impedance measurement may be performed, for example, by controller 110 of FIG. 1.

Continuing to refer to FIG. 3, a decision 320 is made to determine whether the measured pads temperature is greater than the high temperature threshold (e.g., 25° C.). If the answer to decision 320 is YES, then the value of variable pads_temp to be used in the threshold interpolation is set to the high temperature threshold value (e.g., 25° C.) in a step 322. If the answer to decision 320 is NO, then process 300 proceeds to a decision 324, in which a determination is made whether the measured pads temperature is less than the low temperature threshold (e.g., −20° C.). If the answer to decision 324 is YES, then pads_temp is set to the low temperature threshold value (e.g., −20° C.) in a step 326. If the answer to decision 324 is NO, then pads_temp is set to the measured pads temperature value, or a proxy thereof, in a step 328.

From steps 322, 326, and 328, process 300 proceeds to a step 330, in which the impedance threshold value high_level (i.e., the value above which the pads impedance would be considered to be too high for safe usage of the pads) is calculated for the given temperature value of variable pads_temp. The equation used to calculate high_level takes into account the variable pads_temp as set in step 322, 326, or 328.

Still referring to FIG. 3, a determination is made in a decision 340 whether the value of pads impedance measured is above the calculated threshold value high_level from step 330. If the answer to decision 340 is YES, then at step 342, an indication is noted at the AED controller that the pads may be degraded such that they are unsafe for further use. If the answer to decision 340 is NO, then an indication is noted at the AED controller that the pads condition is normal in a step 348. Following step 342 or 348, the operation of AED is adjusted in a step 350 according to whether the pads condition is determined to be degraded or normal. For example, if the condition of the pads are determined to be normal, then an indication may be displayed on the AED or sent to a registered user that a self-test of the pads indicates that the pads condition is normal and that they are ready for use. If the self-test indicates that the pads may be degraded, then an alert may be sent to the registered user to urge replacing the pads as soon as possible or, if the AED is in use for providing an electric shock to a SCA patient, an alert may be displayed in a user interface to warn the user that the pads may be degraded and the AED performance may be compromised. Process 300 is terminated in an end step 360. Process 300 may take place, for example, at controller 110 of AED 100 of FIG. 1.

Additional operations of the AED may be modified based on the temperature measurements and pad impedence measurements described above. For example, thresholds for CPR feedback such as a compression rate threshold and/or a compression depth threshold may be modified. CPR impedence thresholds may also be adjusted based on the temperature and/or pad impedence measurements.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. For instance, AED 100 may further include a global positioning system (GPS) transceiver as part of satellite modem 180. Then, AED 100 may use GPS signals to determine, for instance, the geographical location and altitude, which information may be used in considering the environmental conditions in which the AED is placed, such as described above. Alternatively, GPS data may be obtained using another component in communications block 170, such as cellular modem 172, Bluetooth modem 174, Wi-Fi modem 176, and/or wired connection 178.

Features described above as well as those claimed below may be combined in various ways without departing from the scope hereof. The following examples illustrate some possible, non-limiting combinations:

(A1) An automated external defibrillator (AED) system includes shock generating electronics, a battery configured for providing power to the shock generating electronics, power management circuitry configured for managing the shock generating electronics and the battery, at least one environmental sensor configured for monitoring environmental conditions in which the AED system is placed, and a controller configured for controlling the power management circuitry and the at least one environmental sensor. The at least one environmental sensor includes a temperature sensor configured for providing a temperature measurement, and the controller is further configured for adjusting operations of the power management circuitry in accordance with the temperature measurement provided by the temperature sensor.

(A2) For the AED system denoted as (A1), the power management circuitry may be further configured for measuring a voltage level of the battery, and the controller may be further configured for comparing the voltage level of the battery so measured with at least one voltage threshold level. The voltage threshold level may be selected based on the temperature measurement provided by the temperature sensor.

(A3) For the AED system denoted as (A1) or (A2), a user interface may be configured for displaying information to a user of the AED system. The controller may be further configured for providing an indication at the user interface, in accordance with the voltage level of the battery so measured in comparison with the at least one voltage threshold level.

(A4) For the AED system denoted as any of (A1) through (A3), in accordance with the voltage level of the battery so measured in comparison with the at least one voltage threshold level, the controller may be further configured for instructing the power management circuitry to set a charge rate of the shock generating circuitry.

(A5) For the AED system denoted as any of (A1) through (A4), the controller may be configured for instructing the power management circuitry to reduce the charge rate of the shock generating circuitry when the voltage level of the battery is less than the at least one voltage threshold level.

(A6) For the AED system denoted as any of (A1) through (A5), a wireless charging mechanism may be configured for wirelessly charging the battery. In accordance with the voltage level of the battery so measured in comparison with the at least one threshold level, the power management circuitry may be further configured for initiating a process to charge the battery.

(A7) For the AED system denoted as any of (A1) through (A6), a pair of pads may be provided for transmitting an electric shock from the shock generating electronics to a patient. The controller may be further configured for measuring a face-to-face impedance value between the pair of pads, and the controller may be further configured for comparing the face-to-face impedance value between the pair of pads so measured with at least one impedance threshold level. The impedance threshold level may be selected based on the temperature measurement provided by the temperature sensor.

(A8) For the AED system denoted as any of (A1) through (A7), a user interface may be configured for displaying information to a user of the AED system. The controller may be further configured for providing an indication to the user interface, in accordance with the face-to-face impedance value between the pair of pads so measured in comparison with the at least one impedance threshold level.

(A9) For the AED system denoted as any of (A1) through (A8), the controller may be configured for providing an indication to the user interface when the face-to-face impedance value is greater than the at least one impedance threshold level.

(B1) A method for using an automated external defibrillator (AED) system includes the AED system including shock generating electronics, a battery configured for providing power to the shock generating electronics, power management circuitry configured for managing the shock generating electronics and the battery, at least one environmental sensor for monitoring environmental conditions in which the AED system is placed, and a controller configured for controlling the power management circuitry and the at least one environmental sensor. The method includes measuring a temperature of the AED system, and adjusting operations of the power management circuitry in accordance with the temperature so measured.

(B2) For the method denoted as (B1), the method may include measuring a voltage level of the battery, and comparing the voltage level of the battery so measured.

(B3) For the method denoted as (B1) or (B2), the AED system may further include a user interface, and the method may further include providing an indication at the user interface, in accordance with the voltage level of the battery so compared.

(B4) For the method denoted as any of (B1) through (B3), in accordance with the voltage level of the battery so measured in comparison with the at least one threshold level, the method may include modifying a charge rate of the shock generating circuitry.

(B5) For the method denoted as any of (B1) through (B4), the method may include measuring the temperature of the AED system including one selected from a group consisting of measuring a temperature of the battery, measuring an internal temperature of an AED case, and measuring an environment temperature.

Accordingly, many different embodiments stem from the above description and the drawings. It will be understood that it would be unduly repetitious and obfuscating to literally describe and illustrate every combination and sub-combination of these embodiments. As such, the present specification, including the drawings, shall be construed to constitute a complete written description of all combinations and subcombinations of the embodiments described herein, and of the manner and process of making and using them, and shall support claims to any such combination or sub-combination.

What is claimed is:

1. A method for using an automated external defibrillator (AED) system, the AED system including shock generating electronics, a pair of pads for transmitting an electric shock from the shock generating electronics to a patient, a battery configured for providing power to the shock generating electronics, power management circuitry configured for managing the shock generating electronics and the battery, a temperature sensor configured for providing a temperature measurement, and a controller configured for controlling the power management circuitry and the temperature sensor, the method comprising:

measuring a temperature of the AED system via the temperature sensor, adjusting operations of the power management circuitry in accordance with the temperature measurement provided by the temperature sensor, measuring a face-to-face impedance value between a pair of pads, and comparing the face-to-face impedance value between the pair of pads so measured with at least one impedance threshold level, wherein the impedance threshold level is selected based on the temperature measurement provided by the temperature sensor.

2. The method of claim 1, wherein the AED system includes a user interface, the method comprising:

providing an indication via a user interface when the face-to-face impedance value is greater than the impedance threshold level.

3. The method of claim 1, further comprising:

measuring a voltage level of the battery, and comparing the voltage level of the battery so measured with at least one voltage threshold level adjusted for the temperature so measured.

4. The method of claim 3, wherein the AED system includes a user interface, the method comprising:

providing an indication at the user interface, in accordance with the voltage level of the battery so compared.

5. The method of claim 3, further comprising:

in accordance with the voltage level of the battery so measured in comparison with the at least one threshold level, modifying a charge rate of the shock generating circuitry.

6. The method of claim 5, further comprising:

providing an indication of the charge rate via a user interface.

7. The method of claim 5, further comprising:

instructing the power management circuitry to reduce the charge rate of the shock generating circuitry when the voltage level of the battery is less than the at least one voltage threshold level.

8. The method of claim 1, further comprising:

charging the battery via the power management circuitry, wherein the AED system comprises a wireless charging mechanism configured for wirelessly charging the battery.

* * * * *